US009205234B2

(12) United States Patent
Hardin

(10) Patent No.: US 9,205,234 B2
(45) Date of Patent: Dec. 8, 2015

(54) DEVICE FOR A BIOLOGICAL TREATMENT

(71) Applicant: Terry D. Hardin, Irvine, CA (US)

(72) Inventor: Terry D. Hardin, Irvine, CA (US)

( * ) Notice: Subject to any disclaimer, the term of this patent is extended or adjusted under 35 U.S.C. 154(b) by 317 days.

(21) Appl. No.: 13/851,789

(22) Filed: Mar. 27, 2013

(65) Prior Publication Data

US 2013/0261544 A1   Oct. 3, 2013

Related U.S. Application Data

(60) Provisional application No. 61/616,201, filed on Mar. 27, 2012.

(51) Int. Cl.
*A61M 25/10* (2013.01)
*A61B 17/12* (2006.01)
*A61B 17/3207* (2006.01)
*A61M 25/00* (2006.01)
*A61B 17/22* (2006.01)
*A61B 17/30* (2006.01)
*A61B 17/32* (2006.01)

(52) U.S. Cl.
CPC ...... *A61M 25/1011* (2013.01); *A61B 17/12045* (2013.01); *A61B 17/12109* (2013.01); *A61B 17/12136* (2013.01); *A61B 17/320758* (2013.01); *A61B 2017/22067* (2013.01); *A61B 2017/22082* (2013.01); *A61B 2017/306* (2013.01); *A61B 2017/320004* (2013.01); *A61B 2017/320766* (2013.01); *A61M 2025/0004* (2013.01); *A61M 2025/1015* (2013.01); *A61M 2025/1052* (2013.01)

(58) Field of Classification Search
CPC ................ A61M 25/1011; A61M 2025/0004; A61M 2025/1015; A61B 17/12045; A61B 17/12109; A61B 17/320758
See application file for complete search history.

(56) References Cited

U.S. PATENT DOCUMENTS

| 5,951,514 | A * | 9/1999 | Sahota ..................... 604/101.05 |
| 6,958,059 | B2 | 10/2005 | Zadno-Azizi |
| 7,083,594 | B2 | 8/2006 | Coppi |
| 7,662,143 | B2 | 2/2010 | Carrison et al. |
| 2008/0221552 | A1 | 9/2008 | Leonard |
| 2009/0182227 | A1 | 7/2009 | Goldman |
| 2010/0076365 | A1 | 3/2010 | Riina et al. |
| 2010/0082012 | A1* | 4/2010 | Hattangadi et al. ........... 604/509 |
| 2010/0280595 | A1 | 11/2010 | Bilge et al. |

* cited by examiner

*Primary Examiner* — Nicholas Lucchesi
*Assistant Examiner* — Melissa A Snyder
(74) *Attorney, Agent, or Firm* — Kristin L. Murphy; Brooks Kushman, P.C.

(57) ABSTRACT

A treatment device is disclosed for treating an area within a biological pathway or space. The treatment device includes a catheter that has a first pair of dilation balloons and a second pair of dilation balloons configured to create a sealed treatment area within a vessel. Treatment fluids may be provided to the treatment area via a fluid lumen and fluid may be removed from the treatment area via the same fluid lumen or separate aspiration lumen.

20 Claims, 12 Drawing Sheets

DEVICE FOR A BIOLOGICAL TREATMENT

TECHNICAL FIELD

The disclosure relates to an arrangement for treating an area within a biological pathway or space.

BACKGROUND

Physicians have several treatment methods available to treat various ailments throughout the cardiovascular system and other biological spaces. One exemplary ailment is atherosclerosis, which is a buildup of fatty deposits on the inner walls of vascular lumens. Over time, however, this buildup can lead to stenosis, i.e., narrowing of the vessel, and reduced blood flow. Reduction in blood flow can cause ischemia which can, in turn, manifest itself as angina, stroke, myocardial infarction, hypertension, etc. Various treatments are used to restore blood flow.

One treatment option is bypass surgery, in which a healthy vessel is used to replace the section of vessel where the plaque is occluding flow. This method is highly invasive and requires extensive recuperation.

Exemplary minimally invasive treatment options to address atherosclerosis include angioplasty, stenting, and atherectomy. These methods are all aimed at increasing the diameter of the existing vessel in order to restore or increase blood flow through the occluded section. Angioplasty and stenting involve compressing, or diametrically displacing, the plaque. This displacement of plaque increases the effective diameter of the vessel so that blood flow is improved. A shortfall of angioplasty and stenting is that the treated vessel can re-stenose over time. Restenosis is the result of the biological response caused by mechanical stretching of the vessel that occurs with inflating balloons used in angioplasty and expanding stents. This vessel stretching can also lead to vessel injury, which can in turn cause a vessel to constrict following angioplasty. With the use of stents, intimal thickening can lead to vessel narrowing. Moreover, these known methods do not remove the plaque, but rather simply displace it. In addition, stenting can preclude the use of various treatment options at a future stage and in-stent restenosis can be difficult to treat.

With atherectomy, plaque is removed from the affected vessel by mechanical means, such as sanding or cutting. The challenges with atherectomy methods include the following: unfavorable outcomes in the coronary arteries, limited levels of plaque removal, and potential damage to the artery wall. With limited plaque removal, the potential for restenosis of the artery is significant.

Other exemplary ailments may benefit from treatment devices and/or options throughout the cardiovascular system. As one example, treatment of certain organs or tissue may be accomplished if a vessel (or vessels) that controls blood flow to that area can be isolated to provide targeted and selective delivery of a treatment, as opposed to known systemic treatment options. As another example, it may also be beneficial to have a treatment device that permits isolation of a portion of a heart to treat a calcified heart valve. As yet a further example, it may also be beneficial to isolate a portion of vessel that has an aneurysm to permit removal of blood and/or follow-up treatment.

DETAILED DESCRIPTION

Figure 1:
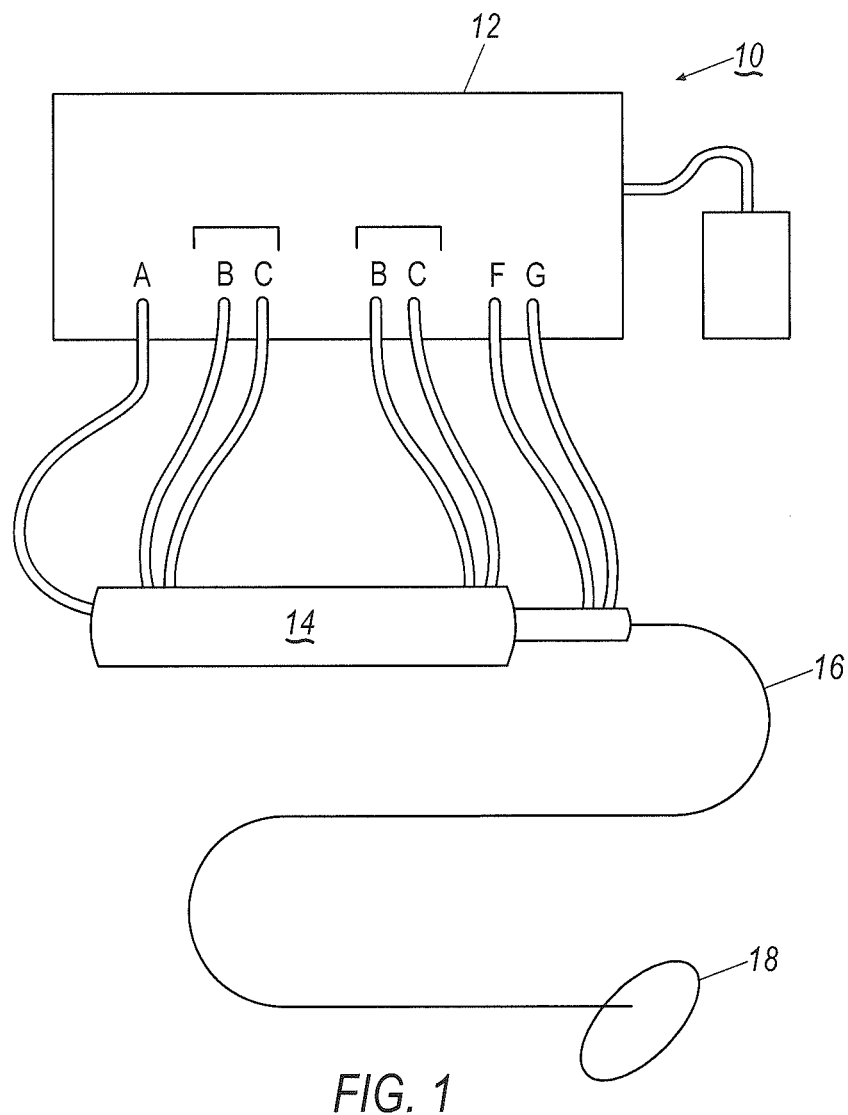
FIG. 1 is a schematic of a surgical system.

A minimally invasive device is proposed that isolates an area of a biological vessel or space. The isolated section of vessel becomes a 'treatment region'. Once the 'treatment region' is created, that portion of the vessel can be dealt with in a variety of ways, including, but not limited to: chemical treatment, therapeutic agent application, 'sanding', ultrasonic energy, angioplasty, stenting, atherectomy, cutting balloon, biologics, stem cell injections, chemotherapy agents, embolic agents, imaging agents, or any combination of the aforementioned.

The advantage of the proposed devices is that the portion of the vessel may be isolated to allow for more robust, thorough treatment. By isolating a portion of the vessel, treatment can be administered without affecting a surrounding portion of vessel or vascular system, thereby permitting more treatment options. For example, chemical(s) and/or therapeutic agent(s) may be delivered at much higher concentrations to the affected area than could typically be administered with conventional devices because the design prevents the substance(s) from traveling downstream or outside of the treatment region.

Similarly, in instances where plaque treatment is called for, more aggressive mechanical approaches can also be taken because any plaque particles generated will not travel downstream and fluids to facilitate the mechanical mechanism of action could be introduced into the treatment region. Further, the proposed devices described herein may also allow plaque to be pre-treated before angioplasty and/or stenting to increase effectiveness of those treatments.

According to one aspect of the disclosure, the proposed designs isolate a treatment region by creating a seal on either side of a portion of a vessel, such as, for example, a diseased portion of the vessel. In one exemplary configuration, vacuum is used to create a seal on the proximal and distal ends of a targeted region, thereby creating the treatment region, while isolating the treatment region from the rest of the vascular system. An embodiment is also proposed whereby the integrity of the seals may be monitored.

According to another aspect of the disclosure, dilation balloons need not be inflated to a point that they are placing unnecessary and potentially damaging stress against the vessel walls. Once the balloons contact the vessel walls, it is proposed to use vacuum to pull the vessel to the balloons to create a seal. Further, the vacuum level may be monitored as a check on the seal integrity. Without the use of vacuum, the balloons would need to exert force on the vessel walls and stretch them in hopes of creating a seal. The proposed vacuum method ensures that a seal is created and reduces the likelihood of barotrauma or vessel dissection.

The proposed catheters and system disclosed herein involve the use of a minimally invasive catheter device that's introduced into the vascular system through standard percutaneous access techniques. The device is then delivered to the target area through the vasculature with accepted imaging and interventional techniques. In some exemplary arrangements, the device may contain radiopaque markings to assist with proper positioning of the catheter within the vasculature.

Turning now to the drawings, a detailed explanation of the various exemplary arrangements will be described.

FIG. 1 illustrates an exemplary surgical system 10. Surgical system 10 includes a console 12, a handpiece 14 and a catheter device 16. The console 12 provides a mechanism for dilating balloons (to be described below). In one configuration, console may include one or more of a compressor and/or pump to dilate the balloons. In another arrangement, an external mechanism for dilating balloons may be employed, such as a syringe. In yet a further arrangement, the catheter device 16 may utilize an adapter in lieu of a console 12/handpiece 14. The adapter has a plurality of ports operatively connected thereto may be used for controlling dilation of balloons, as well as other actions. The adapter configuration will be described in further detail below in connection with FIG. 15. Console 12 also include a vacuum source to pull vacuum between catheter balloons and to aspirate a treatment area. In another arrangement, an external mechanism for generating vacuum may be employed, such as a syringe. Console 12 may also include a pump for blood flow. Handpiece 14 provides for connections between console 12 and catheter device 16. A fluid source 15 may be operatively connected to the console 12. The fluid source 15 may be any fluid, such as for flushing a treatment area, or may be a therapeutic fluid to apply a treatment to the treatment area. As may be seen in FIG. 1, the console 12 further includes fluid lines that operatively connect to the catheter device 16, through the handpiece 14. Such fluid lines include, but are not limited to, a blood flow line A, at least one balloon dilation line B, D, at least one vacuum line C, E, associated with the dilation balloons, a fluid delivery line F, and an aspiration line G.

Figure 2:
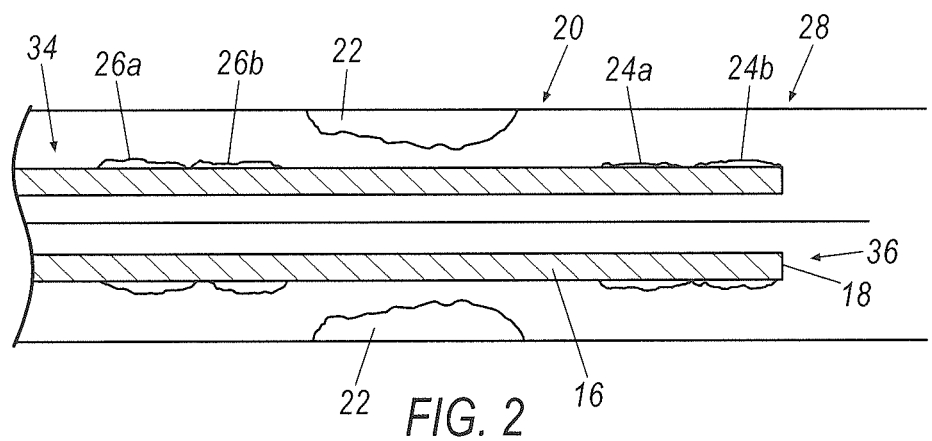
FIG. 2 is a partial cross-sectional view of a catheter device used with the system of FIG. 1, advanced through vasculature at an area of interest of a vessel wall.

Turning to FIG. 2, a distal end 18 of catheter device 16 is delivered through a vessel 20 until it reaches the site of a target area 22. In one exemplary arrangement, the target area 22 may be a lesion, such as plaque. However, it is understood that the present disclosure is not limited to treatment devices used to apply treatments to lesions and/or plaque. Thus, any references to a lesion and/or plaque treatment are merely exemplary and non-limiting.

Once at the site of the target area 22, distal end 18 of catheter device 16 is delivered across the target area 22 such that a pair of distal balloons 24a, 24b located adjacent distal end 18 are spaced distally of target area 22. A pair of proximal balloons 26a, 26b are positioned proximally of target area 22. As will be explained in further detail below, the section of vessel 20 containing target area 22 will be isolated from the rest of the vascular system by the use of multiple balloons 24a-24b and 26a-26b.

Figure 3:
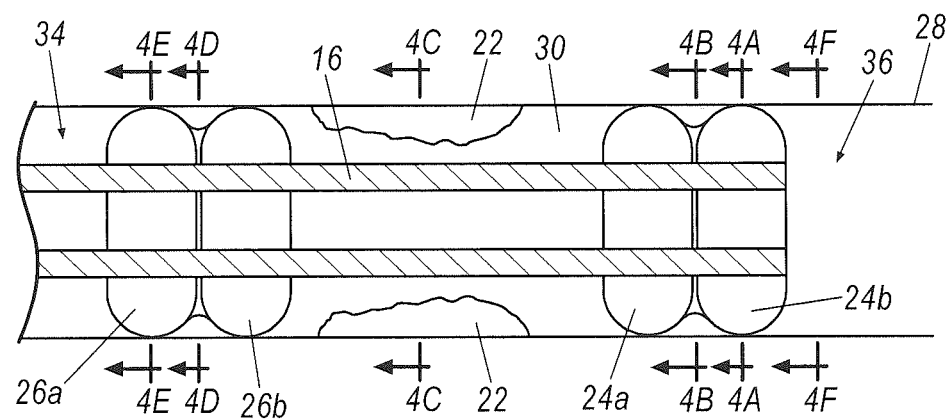
FIG. 3 is a partial cross-sectional view of the catheter device of FIG. 2, with proximal and distal balloons being dilated to contact the vessel wall.
Figure 4A:
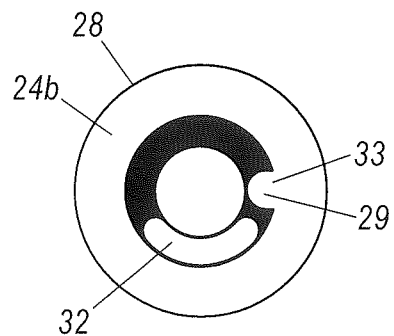
FIG. 4A is a cross-sectional view taken along lines A-A in FIG. 3.

More specifically, distal balloons 24a-24b will be positioned distal to the target area 22 and two proximal balloons 26a-26b will be positioned proximal to the target area 22. The balloons 24a-24b and 26a-26b on either side of the target area 22 will be dilated, as shown in FIG. 3, either at the same time or separately, so as to contact the vessel wall 28. In one exemplary configuration, catheter 16 may be designed so that the balloons 24a-24b, 26a-26b dilate to the same pressure. Alternatively, catheter 16 may be configured such that balloons 24a-24b, 26a-26b dilate to different pressures if needed. While balloons 24a-24b, 26a-26b are illustrated as having the generally same size and shape, it is understood that the disclosure is not so limited. For example, balloons 24a-24b, 26a-26b may have different shapes, as well as different sizes. It is understood that one or more lumen(s) 29 will control balloon dilation and deflation. For example, referring to FIG. 4A, opening 33 is provided to allow communication between lumen(s) 29 and balloon 24b.

In one exemplary configuration, one or more portions of catheter 16 may be provided with a marker element (not shown) to assist in delineating the position of catheter 16 under imaging. The marker elements may be provided in any suitable form, including, but not limited to, radiopaque bands or other suitable marker elements. The marker element(s) may be disposed adjacent dilation balloons 24a-24b and 26a-26b to assist in locating balloons 24a-24b and 26a-26b in relation to a target area 22. In one exemplary configuration, at least one marker element may be disposed on catheter 16 proximally of dilation balloon 24a, and a least one marker element may be disposed on catheter 16 distally of dilation balloon 26b. In this manner the projected target area 22 may be visualized to allow for proper placement of the dilation balloons 24a-24b and 26a-26b.

Figure 4B:
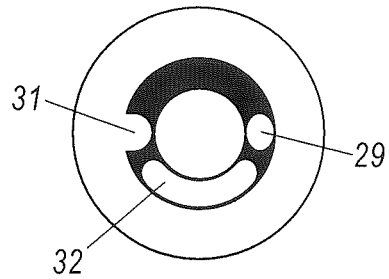
FIG. 4B is a cross-sectional view taken along lines B-B in FIG. 3.

Once positioned at the site of target area 22 and the balloons are dilated, vacuum may be delivered between the two distal balloons 24a-24b, located on the distal end 18 of catheter 16, through lumen 31, and between the two proximal balloons 26a-26b located on the proximal side of the target area 22. An opening 35 is provided to allow communication between lumen 31 and gap between balloons 26a-26b. An opening (shown in FIG. 4B) is also provided to allow communication between lumen 31 and gap between balloons 24a 24b. The vacuum is configured to ensure that a seal is created between the balloons and the vessel wall. Vacuum can be applied between the distal set of balloons 24a-24b and between the proximal set of balloons 26a-26b at the same time or sequentially. The seals created between distal balloons 24a-24b and proximal balloons 26a-26b thereby create a treatment region/chamber 30 within vessel 20, thereby readying the vessel 20 for treatment.

As described above, in one exemplary arrangement, system 10 is driven by console 12 and/or handpiece 14 that is external to the patient. In this exemplary arrangement, these devices permit control of the vacuum, the delivery of fluids, aspiration, and the monitoring of pressure within the device 16 and the vessel 20. More specifically, vacuum can be monitored within the treatment region 30 (i.e., between distal balloons 24a, 24b and proximal balloons 26a, 26b) to ensure that a suitable seal is achieved and maintained.

However, as will be explained in further detail below, in lieu of a console 12 and handpiece 14, a proximal end of the catheter 16 may contain an adapter with infusion, dilation, aspiration, and vacuum ports. In such an arrangement, gauges may be operatively connected to such ports to provide pressure/vacuum monitoring.

As may be seen in FIGS. 4A-4F, catheter 16 contains one or more lumen(s) 32 which allow blood to flow from a proximal portion 34 of the vascular system (shown in FIG. 2) (and/or from the console 12), through the catheter device 16, and then into the distal portion 36 of the vessel 20 so as to not compromise blood flow through the vascular system. In one exemplary arrangement, catheter 16 may contain a dedicated blood flow lumen. Alternatively, a guidewire lumen 32a may also serve as a blood flow lumen when the guidewire is removed. Handpiece 14 or console 12 may also be provided with a pump (not shown) to assist with blood flow control through catheter device 16 to a distal portion 36 of the vessel.

Figure 4C:
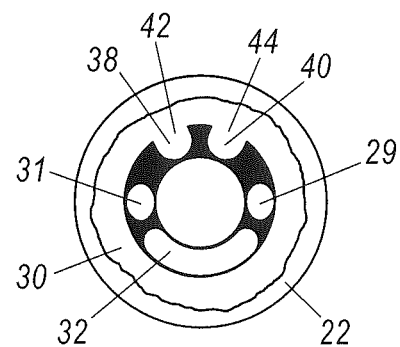
FIG. 4C is a cross-sectional view taken along lines C-C in FIG. 3.
Figure 4D:
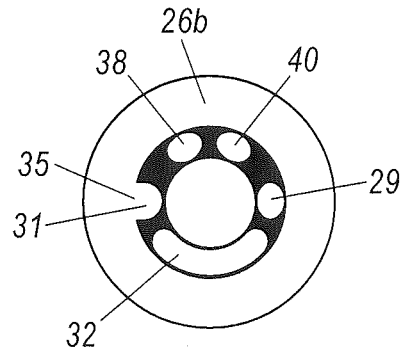
FIG. 4D is a cross-sectional view taken along lines D-D in FIG. 3.
Figure 4E:
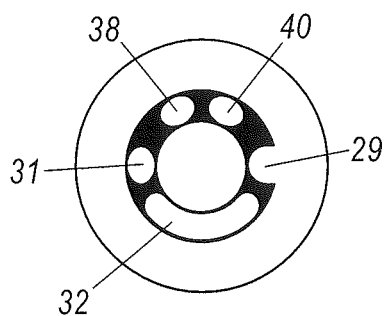
FIG. 4E is a cross-sectional view taken along lines E-E in FIG. 4.
Figure 4F:
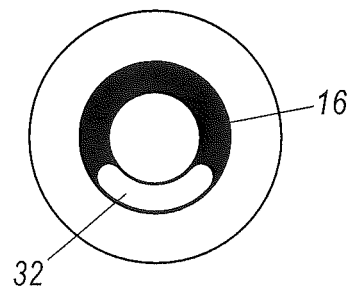
FIG. 4F is a cross-sectional view taken along lines F-F in FIG. 4.

As best seen in FIGS. 4C-4E, catheter device 16 also contains one or more lumen(s) 38 for aspirating the treatment region 30 and one or more lumen(s) 40 for delivering fluid into the treatment region 30. While depicted as using two separate lumens for aspiration and fluid delivery, it is understood that alternatively, a single lumen may be used for both fluid introduction and aspiration. Openings 42, 44 are provided to permit communication between treatment region 30 and lumens 38, 40. Aspirating the treatment region 30 via vacuum through the aspiration lumen(s) 38 will in turn pull fluid into the treatment region 30 through the fluid delivery lumen(s) 40. Aspirating treatment region 30 allows for removal of blood from treatment region 30, as well as the introduction of fluid(s) to facilitate treatment. In another arrangement, handpiece 14 or console 12 may be provided with a pump (not shown) to deliver fluid into the treatment region 30 through the fluid delivery lumen(s) 40.

The aspiration lumen(s) 38 and fluid delivery lumen(s) 40 will communicate with the treatment region 30 via openings 42, 44 in the catheter device 16. The openings 42, 44 in the device 16 can be placed at various positions within the treatment region 30 to optimize fluid flow and treatment. It is understood that multiple openings may be employed.

In one exemplary arrangement, any fluid introduced into the treatment region 30 may be allowed to dwell for a predetermined period of time, continuously flushed, or pulsated. Fluids can include any combinations of chemicals, drugs, cleaning agents, ultrasonic cleaning agents, blood, suspensions, imaging agents, embolic agents, chemotherapy agents, thrombolytic agents, stem cells, enzymes, biologics, etc. that may be employed to facilitate or perform treatment.

Once the vessel 20 is treated, which may be confirmed by standard imaging techniques, blood may be re-introduced into the treatment region 30, the seals may be collapsed (i.e., dilation balloons 24a-24b, 26a-26b), and the device removed from the patient.

For one particular arrangement, where a lesion, such as a plaque region 22 disposed within a vessel is to be treated, there are a variety of treatment options, which include, but are not limited to the following:

Introduction of chemicals. By isolating the plaque region 22 from the rest of the vascular system, chemicals can be introduced into the treatment region 30 without concern over the chemicals spreading into the rest of vascular system. Catheter 16 is configured such that the chemical(s) are pulled into treatment region via the fluid delivery lumen(s) 40. The chemical(s) may be selected so as to dissolve the plaque and/or break it away from the vessel wall 28 and/or prepare the plaque for mechanical treatment and/or provide the vessel wall 28 with therapeutic substances. Chemicals may include, but are not limited to, organic solvents, aqueous buffers, enzymes, etc.

In another exemplary arrangement, therapeutic agents(s) may be employed. Drug(s) and/or biologic(s) and/or pharmaceutical(s) and/or nanotechnology based molecules and/or enzymes could be delivered directly to the plaque 22 and/or vessel wall 28 through the fluid delivery lumen(s) 40. The therapeutic agent(s) would be delivered into treatment region 30 via the fluid delivery lumen(s) 40. The therapeutic agent(s) would dissolve the plaque 22 and/or break it away from the vessel wall 28 and/or prepare the plaque for mechanical treatment and/or facilitate a mechanical method of treatment and/ or provide the vessel wall 28 with therapeutic substances and/or promote healing and/or prevent restenosis.

Mechanical methods of treatment could include, but aren't limited to, angioplasty, stenting, "sanding", atherectomy, cutting balloons, or any combination of the aforementioned. With angioplasty, an additional balloon element (not shown) may be integrated into the catheter device and would be located between the distal set 24a-24b and proximal set of balloons 26a-26b. The additional balloon element could be controlled by a balloon dilation lumen(s) in the catheter. Similarly, a stent may be integrated into the catheter device and would be located between the distal set and proximal set of balloons 24a-24b and 26a-26b, respectively.

Ultrasonic energy may also be employed. Ultrasonic energy can be applied to exploit the difference in the mechanical properties between plaque 22 and the vessel 20 to break up the plaque 22 into particles which can then be aspirated. With the design of the device 16, fluids could be introduced into the treatment region to facilitate the effectiveness of the ultrasonic energy.

Figure 5:
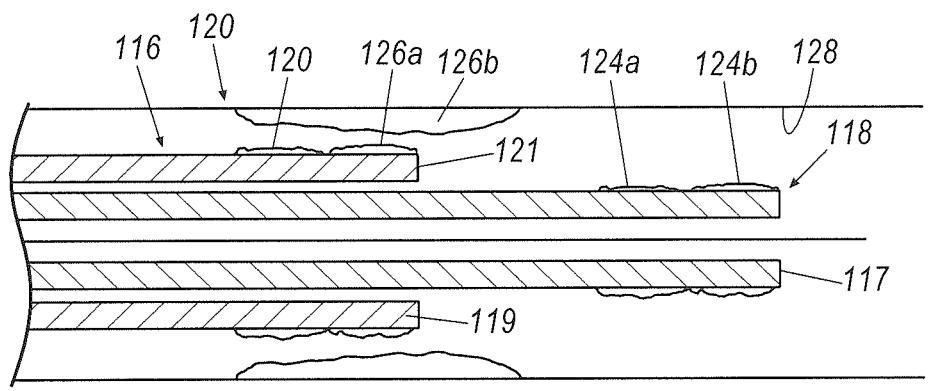
FIG. 5 is a partial cross-sectional view of an alternative arrangement of a catheter device, advanced through the vasculature at an area of interest of a vessel wall.
Figure 6:
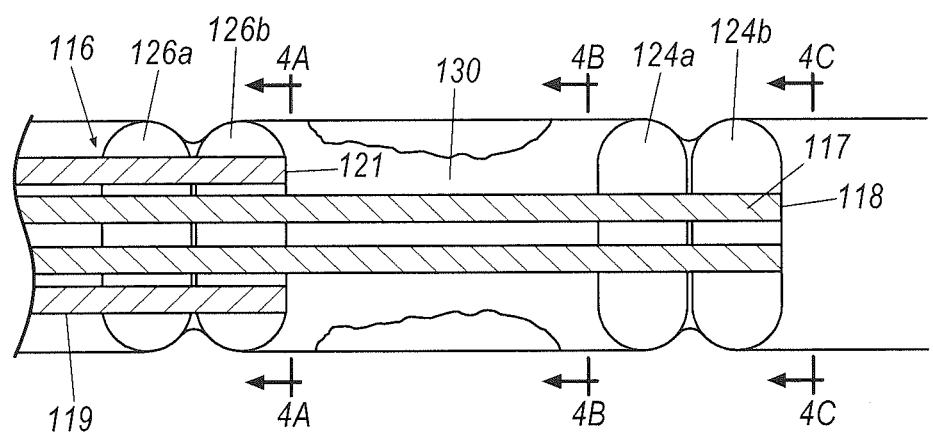
FIG. 6 is a partial cross-sectional view of the catheter device of FIG. 5, with proximal and distal balloons being dilated to contact the vessel wall.

An alternative arrangement of a catheter device 116 that may be used as part of system 10 is shown in FIGS. 5-6. Catheter device 116 includes a first catheter 117 and a second catheter 119. First catheter 117 includes distal balloons 124a-124b similar to distal balloons 24a-24b. Distal balloons 124a-124b are positioned adjacent distal end 118. Second catheter 119 includes proximal balloons 126a-126b similar to proximal balloons 26a-26b. Proximal balloons 126a-126b are positioned adjacent a distal end 121 of second catheter 119.

In operation, catheter device 116 may be delivered in the same manner as catheter device 16 to a treatment site. More specifically, catheter device 116 may be advanced through the vasculature until first catheter 117 is positioned distally to a desired area, such as, for example a plaque region 122. As with device 16, marker elements may be provided on first and second catheters 117, 119 to indicate the proper position of catheter device 116 in vessel 120. Once first catheter 117 is positioned, second catheter 119, which is configured to move independently of first catheter 117, is positioned proximally to a desired target area 122.

Alternatively, second catheter 119 may be positioned proximally first, with the distal end of first catheter 117 disposed in, co-planar, or protruding from the distal end of the second catheter 119. Once so positioned, the first catheter 117 may then be advanced distally relative to the second catheter 119 until the first catheter 117 is positioned distally to target area 122 to define the treatment region 130. Due to the ability to independently move and slide first and second catheters 117, 119, the length of the treatment region 130 may be customized.

Once both the first and second catheter 117, 119 are positioned, distal and proximal balloons 124a-124b and 126a-126b are then dilated via dilation lumens. It is understood that the balloons may be dilated together or sequentially. It is also understood that the each balloon may have a different size and/or shape than the other balloons and what is depicted in the drawings. Once dilated, vacuum is then delivered between distal balloons 124a-124b and between proximal balloons 126a-126b so as to create a sealed treatment region 130, as described above. The use of first and second catheters 117 and 119 permits the user to selectively vary the size and length of treatment region 130.

Figure 7A:
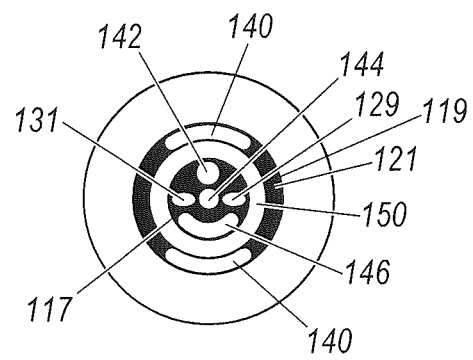
FIG. 7A is a cross-section of the catheter device taken along lines A-A of FIG. 6.
Figure 7B:
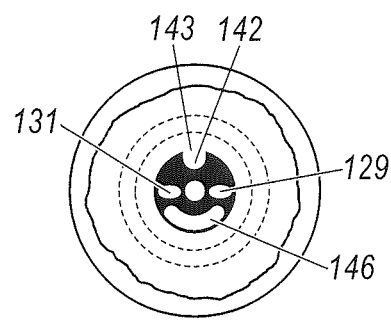
FIG. 7B is a cross-section of the catheter device taken along lines B-B of FIG. 6.
Figure 7C:
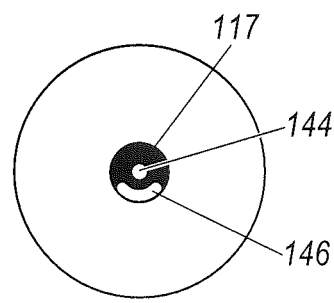
FIG. 7C is a cross-section of the catheter device taken along lines C-C of FIG. 6.

Distal end 121 of second catheter 119 and a cross-section of first catheter 117 is illustrated in FIG. 7A. Second catheter 119 may be provided with one or more lumens 140 that may be used as fluid delivery channels and/or aspiration channels. As may be seen in FIGS. 5 and 6, second catheter 119 also has a lumen for receiving first catheter 117. This configuration permits first and second catheters 117/119 to slide relative to one another. Second catheter 119 may be provided with additional lumens (not shown) to control dilation and deflation of proximal balloons 126a-126b, and to allow a vacuum to be delivered between the two proximal balloons 126a-126b. First catheter 117 may be provided with one or more lumens 142 that may also serve as fluid delivery channels and/or aspiration channels, as shown in FIG. 7B. In one exemplary configuration, additional lumens 129, 131 may be provided to control dilation and deflation of distal balloons 124a-124b, and to allow a vacuum to be delivered between the two distal balloons 124a-124b. Openings (not shown) are provided to allow for the communication between lumen 129 and balloons 124a-124b, and lumen 131 and a gap between balloons 124a and 124b. First catheter 117 is also provided with a guidewire lumen 144, and may also contain a blood flow channel 146, as shown in FIG. 7C. While guidewire lumen 144 is depicted as being centrally disposed, it is understood that the guidewire lumen 144 may be positioned in other locations. Alternatively, catheter 119 may contain the guidewire lumen.

Treatment region 130 may be aspirated and supplied with fluid in a variety of ways. Lumens 140 that open into the treatment region 130 through opening(s) in the distal end or along the length of the catheter 119, which may serve as aspiration and/or fluid delivery channels. Additionally, or alternatively, a gap 150 between first and second catheters 117, 119 may be used as a fluid delivery channel. Catheters 117/119 may contain a seal to prevent fluid from escaping the treatment region 130 into the space between the catheters 117/119.

In one exemplary configuration, first catheter 117 may also contain an aspiration and/or fluid delivery channel 142. In this arrangement, an opening (or openings) 143 must be provided in the catheter 117 to permit communication between the channel and the treatment region 130.

Blood flow through the vascular system when catheter device 116 is used may be maintained by a blood flow channel 146. Alternatively, or in addition, the guidewire lumen 144 may also be used.

Figure 8:
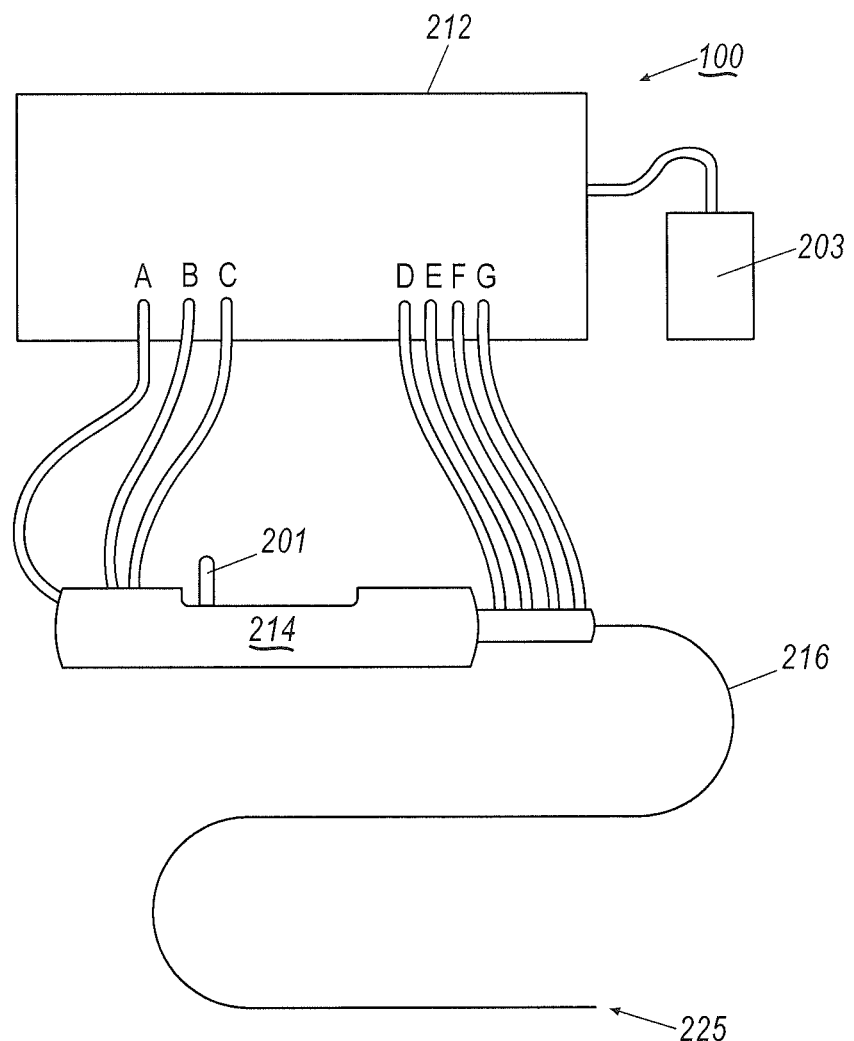
FIG. 8 is a schematic of a surgical system employing the catheter device of FIGS. 5-7.
Figure 9:
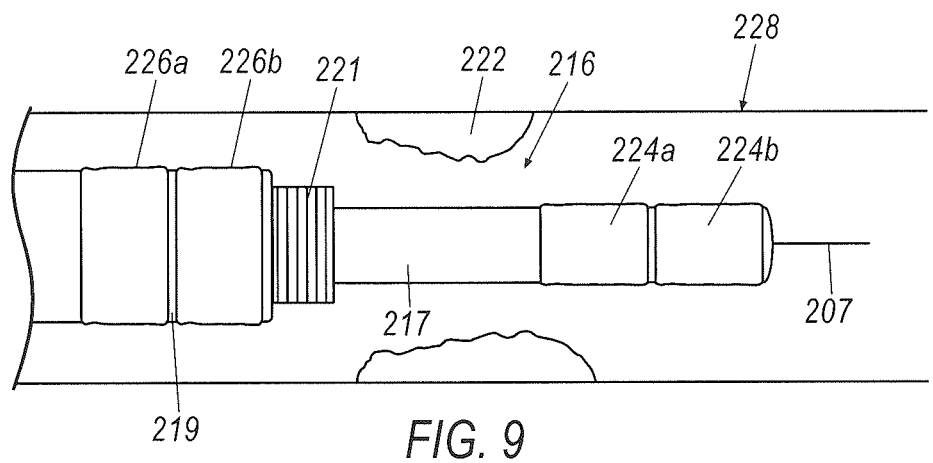
FIG. 9 is an elevational view of an alternative arrangement of a catheter device, advanced through the vasculature at an area of interest of a vessel wall.

FIG. 8 depicts a system 100 that employs a catheter device 216 that is similar to catheter device 116. System 100 may also include a console 212 and a handpiece 214, in addition to catheter device 216. In the exemplary arrangement shown, there are separate control sets for each of first and second 217 and 219 catheters. Console 212 may house an ultrasound signal generator, and a dilation mechanism for the distal and proximal balloons 224a-224b and 226a-226b, respectively. The dilation mechanism may be any suitable arrangement, including, for example, a compressor or a pump. Alternatively, an external mechanism for dilating balloons may be employed, such as a syringe. Console 212 may also include a vacuum generator that is used to pull vacuum between catheter balloons 224-226 and to aspirate the treatment area 230. In another arrangement, an external mechanism for generating vacuum may be employed, such as a syringe. Console 212 may also be provided with a pump for controlling blood flow through catheter device 216. Handpiece 214 may be configured with a motor to rotate a drive shaft 221 (shown in FIGS. 9-11), as will be explained in further detail below. Handpiece 214 may further comprise a lever 201 to permit selective advancement of drive shaft 221. A fluid source 203 that is operatively connected to catheter 216, via console 212, may also be provided. Fluid from fluid source 203 may be selectively delivered to treatment area 230.

As will be explained below, an adapter with ports for controlling the balloons, vacuum, aspiration, and fluid delivery may be used with catheter 216, as opposed to the handpiece/console arrangement depicted in FIG. 8.

Details of catheter device 216 are shown in FIGS. 9-12. More specifically, catheter device 216 is similar to catheter device 116 in that catheter device 216 includes first and second catheters 217 and 219, respectively. First catheter 217 carries distal balloons 224a-224b and second catheter 219 carries proximal balloons 226a-226b. Catheter device 216 further includes a driveshaft 221 that is positioned between first and second catheters 217, 219.

In one exemplary operation, catheter device 216 may be advanced through the vasculature until first catheter 217 is positioned distally of a target area 222, while second catheter 219 remains positioned proximally of target area 222. First catheter 217 may be directed to the desired location using standard imaging techniques and over a guidewire 207 that is configured to extend through a guidewire channel. In some exemplary embodiments, catheter device 216 may be provided with marker elements that are imageable so as to facilitate positioning of first catheter 217.

It is understood that the order of deployment of first and second catheters 217/219 described above is not required. As described above in connection with catheter 116, second catheter 219 may be placed first, followed by first catheter 217. It is also understood that first and second catheter 217/

219 that may be selectively slidable with respect to each other, so as to provide customized target areas.

Figure 10:
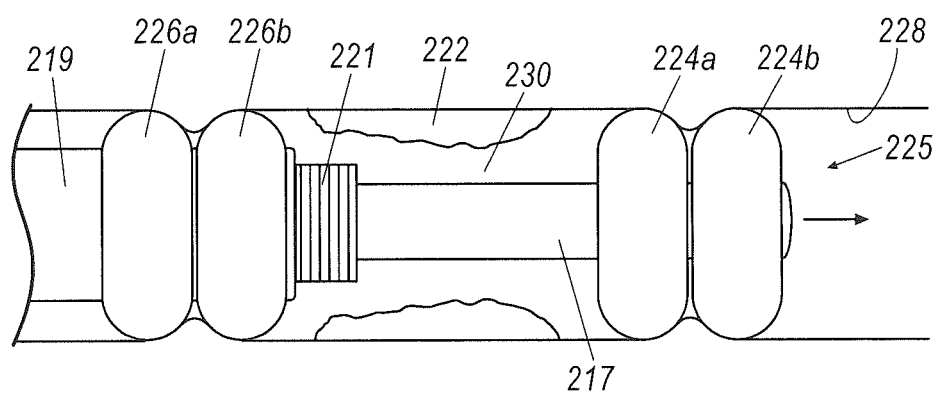
FIG. 10 is an elevational view of the catheter device of FIG. 9 with proximal and distal balloons being dilated to contact the vessel wall.

Referring to FIG. 10, once first and second catheters 217, 219 are appropriately positioned on either side of target lesion/plaque 222, distal balloons 224a, 224b and proximal balloons 226a, 226b are dilated to reach vessel wall 228. As with the other embodiments, balloons 224a, 224b, 226a, and 226b may be dilated at the same time, or sequentially. After dilation, vacuum is delivered in a gap positioned between distal balloons 224a, 224b, and a gap positioned between proximal balloons 226a, 226b, thereby pulling vessel wall 228 toward balloons 224, 226, thereby creating a seal between distal balloons 224a, 224b and vessel wall 228, as well as creating a seal between proximal balloons 226a, 226b and vessel wall 228. The two seals cooperate to create a sealed treatment area 230.

Figure 11:
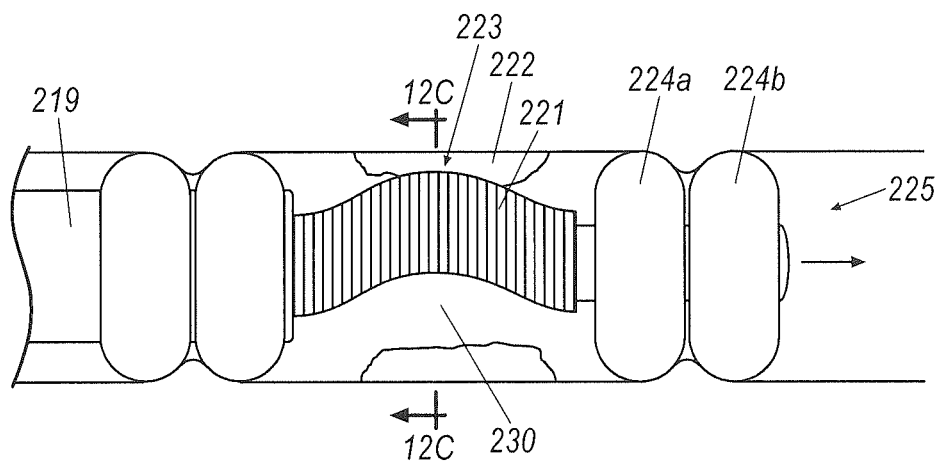
FIG. 11 is an elevational view of the catheter device of FIG. 9, with a driveshaft extended into a treatment area.
Figure 12:
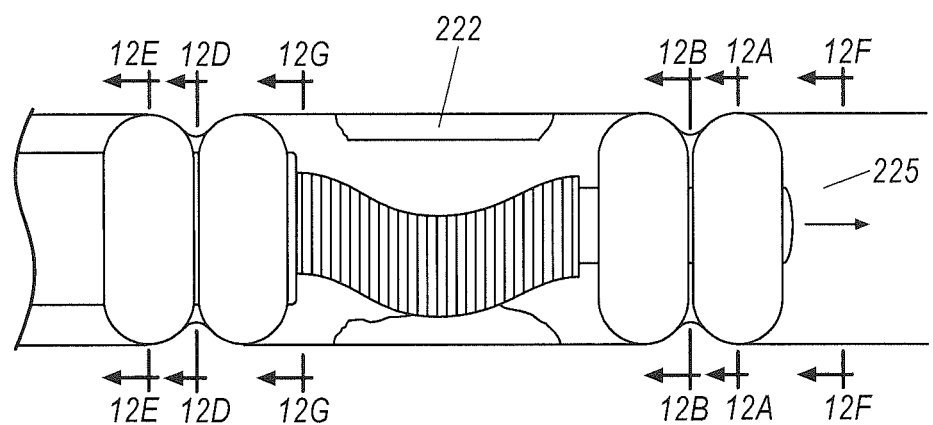
FIG. 12 is an elevational view of the catheter device of FIG. 9, with the driveshaft rotated within the treatment area.

Turning to FIGS. 11-12, details of driveshaft 221 will now be explained. In one exemplary configuration, driveshaft 221 includes a bend or bias 223. The distal end of driveshaft 221 may contain an abrading component or cutting component. Thus, when driveshaft 221 is advanced distally through treatment area 230 (i.e, through activation of lever 201), bend 223 flexes radially to contact target lesion/plaque 222. Further, as discussed above, handpiece 214 may also be provided with a motor (not shown) that rotates driveshaft 221. Thus, the rotation of driveshaft 221, coupled with bend 223 serves to abrade or sand target lesion/plaque 222, as shown in FIGS. 13H-13M. Alternatively, or addition to, the driveshaft 221 could be differently weighted to one side so that rotation by the motor (not shown) causes centrifugal outward motion of the driveshaft radially to contact target area 222. Driveshaft 221 may also be configured such that its rotation serves to mix the fluid that gets delivered into the treatment region in order to facilitate treatment.

While target lesion/plaque 222 is abraded, treatment area 230 may be aspirated via an aspiration lumen 238 (see FIGS. 13D-E and G) in second catheter 219. Aspiration also pulls fluid into treatment region from fluid supply 203 via a fluid supply lumen 240 (see FIGS. 13D-E and G). In another arrangement, handpiece 214 or console 212 may be provided with a pump (not shown) to deliver fluid into the treatment region 230 through the fluid delivery lumen(s) 240. In one exemplary arrangement, the fluid supplied from fluid supply 203 may be configured to dissolve the plaque and/or facilitate its breakdown into particles upon application of the rotating drive shaft 221.

Figure 13A:
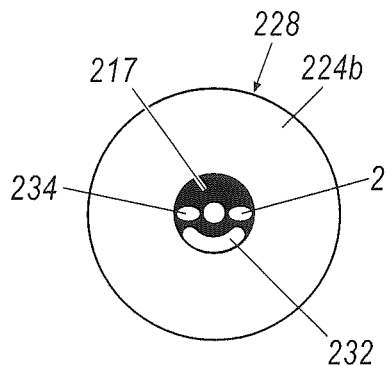
FIG. 13A is a cross-sectional view of the catheter device of FIG. 9 taken along lines A-A of FIG. 12.

Turning now to FIGS. 13A-13G, the various pathways of catheter 216 will be described. A cross-section of first catheter 217 is illustrated in FIG. 13A. As may be seen, device 216 contains one or more lumen(s) 232 which allows blood to flow from a proximal portion of the vascular system (and/or from the console 212), through the catheter device 216, and then into the distal portion of the artery/vessel 225 so as to not compromise blood flow through the vascular system. Handpiece 214 or console 212 may also be provided with a pump (not shown) to assist with blood flow control through catheter device 216 to a distal portion of the vessel. One or more lumens 234 serve to dilate balloons 224/226. A vacuum channel 236 is also provided in each of first and second catheters 217, 219.

Figure 13B:
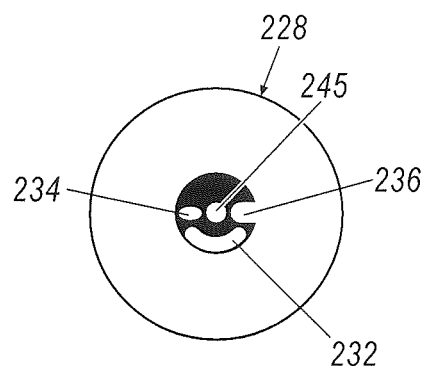
FIG. 13B is a cross-sectional view taken along lines B-B of FIG. 12.
Figure 13C:
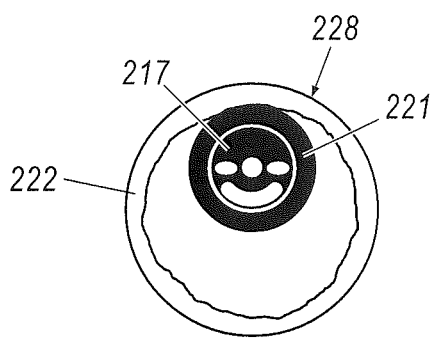
FIG. 13C is a cross-sectional view taken along lines C-C of FIG. 11.
Figure 13D:
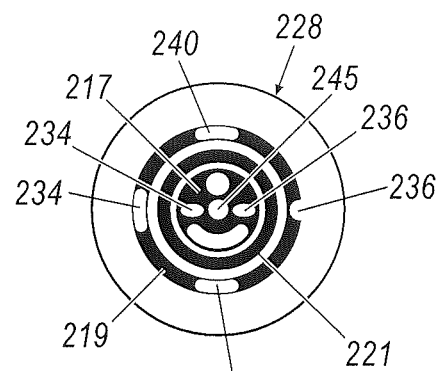
FIG. 13D is a cross-sectional view taken along lines D-D of FIG. 12.
Figure 13E:
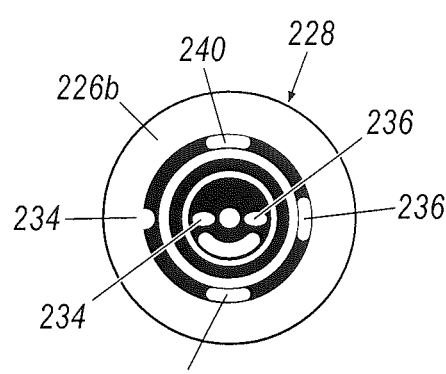
FIG. 13E is a cross-sectional view taken along lines E-E of FIG. 12.
Figure 13F:
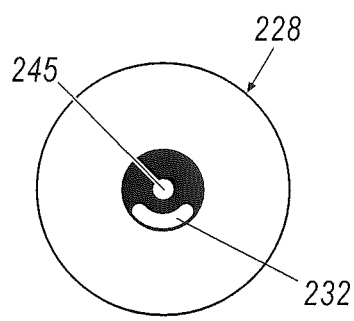
FIG. 13F is a cross-sectional view taken along lines F-F of FIG. 12.
Figure 13G:
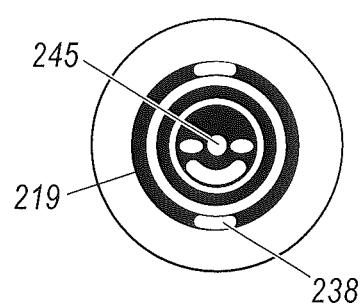
FIG. 13G is a cross-sectional view taken along lines G-G of FIG. 12.
Figure 13H:
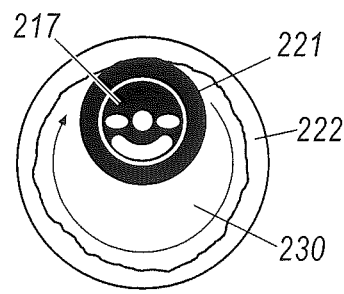
FIG. 13H-13M illustrates a cross-sectional view of a treatment area, illustrating movement of a driveshaft within the treatment area.
Figure 13I:
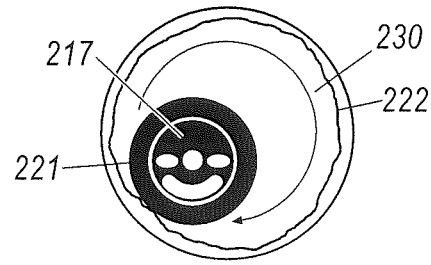
Figure 13J:
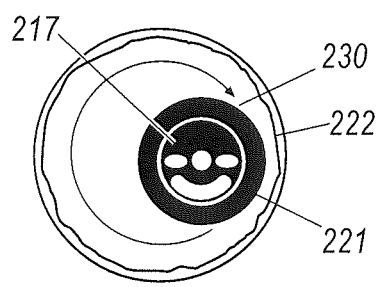
Figure 13K:
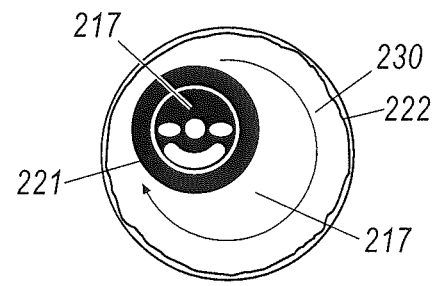
Figure 13L:
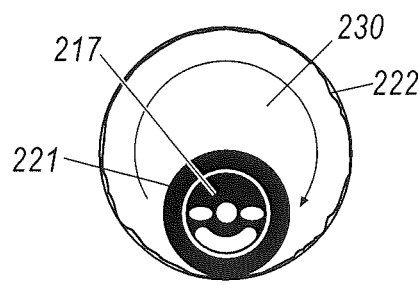
Figure 13M:
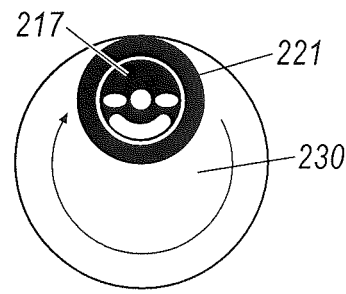

As best seen in FIGS. 13B and 13D-E, catheter device 216 also contains one or more aspiration lumen(s) 238 for aspirating the treatment region 230 and one or more lumen(s) 240 for delivering fluid into the treatment region 230. Alternatively, a single lumen may be used for both fluid delivery and aspiration. Openings are provided to permit communication between treatment region 230 and lumens 238, 240. Aspirating the treatment region 230 via vacuum through the aspiration lumen(s) 238 will in turn pull fluid into the treatment region 230 through the fluid delivery lumen(s) 240. Aspirating treatment region 230 allows for removal of blood from treatment region 230, as well as the introduction of fluid(s) to facilitate treatment.

The aspiration lumen(s) 238 and fluid delivery lumen(s) 240 will communicate with the treatment region 230 via openings in the catheter device 216. The openings in the device 216 can be placed at various positions within the treatment region 230 to optimize fluid flow and treatment. It is understood that multiple openings may be employed.

In one exemplary arrangement, any fluid introduced into the treatment region 230 may be allowed to dwell for a pre-determined period of time, continuously flushed, or pulsated. Fluids can include any combinations of chemicals, drugs, cleaning agents, ultrasonic cleaning agents, blood, suspensions, imaging agents, biologics, enzymes, stem cells, etc. that may be employed to facilitate or perform treatment.

Once the vessel is treated, which may be confirmed by standard imaging techniques, blood may be re-introduced into the treatment region 230, the seals may be released, balloons collapsed, and the device removed from the patient.

Blood flow channel 232 is also provided to permit blood to flow through catheter device 216. In another arrangement, the guidewire lumen 245 could be used for blood flow.

In addition to driveshaft 221, it is also contemplated that other mechanical abrasion or sanding devices may be utilized with any of the catheters disclosed herein. Further, cutting devices, such as atherectomy devices and cutting balloons may also be utilized. In addition, angioplasty and/or stenting may be employed to open a constricted passage. Ultrasonic energy may also be used. Alternatively, any combination of these devices may be used.

Figure 14A:
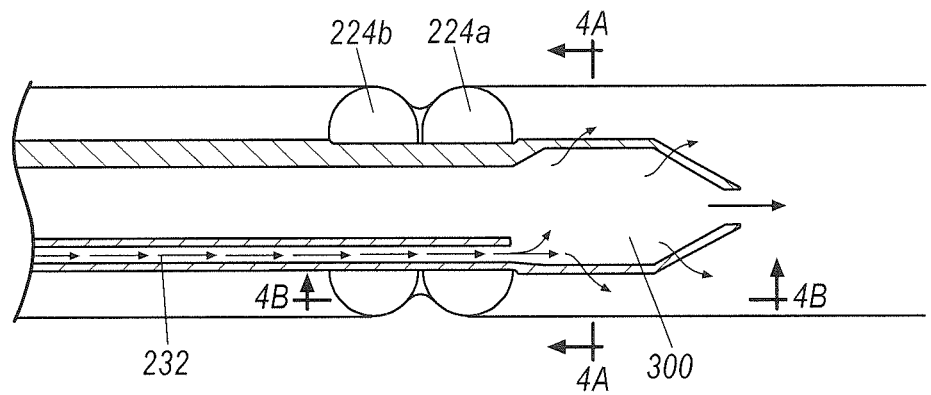
FIG. 14A illustrates an exemplary configuration of a blood flow transition region.
Figure 14B:
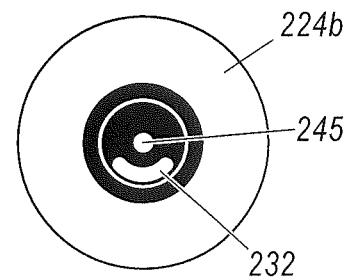
FIG. 14B is a cross-sectional view of the catheter device of FIG. 14A taken along lines B-B of FIG. 14A.
Figure 14C:
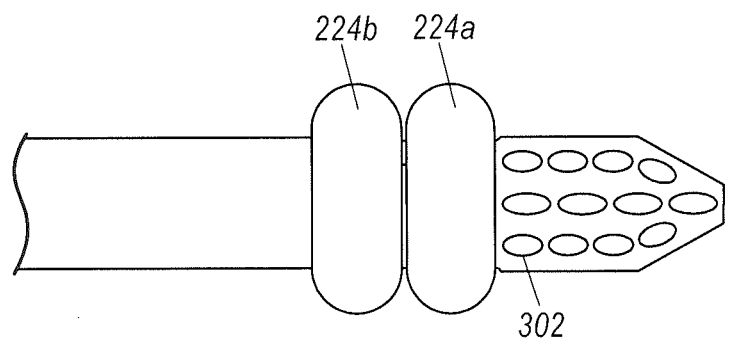
FIG. 14C is a cross-sectional view taken along lines C-C.

The distal end of the catheter device may also be designed such that it creates a blood flow 'transition region' 300 between the blood flow lumen(s) 232 and the vessel (see, e.g., FIG. 14A-14C). The transition region 300 serves to slow down the flow of blood coming out of the blood flow lumen(s) 232 before entering the vessel. Because the blood flow lumen(s) 232 will likely be smaller in diameter and cross section than the vessel, blood may need to be pumped/moved through the lumens at a relatively high velocity (compared to the velocity with which it moves through the vasculature) in order to supply enough blood volume to the distal portion of the vessel so as to not cause ischemia or any increased ischemia in the downstream vasculature. Allowing the blood flow lumen(s) to open directly into the vessel may cause turbulent flow, which is undesirable in vessels. As shown in FIG. 14C, transition region 300 includes a plurality of holes 302 to assist in dispersing and reducing turbulent flow.

Figure 15:
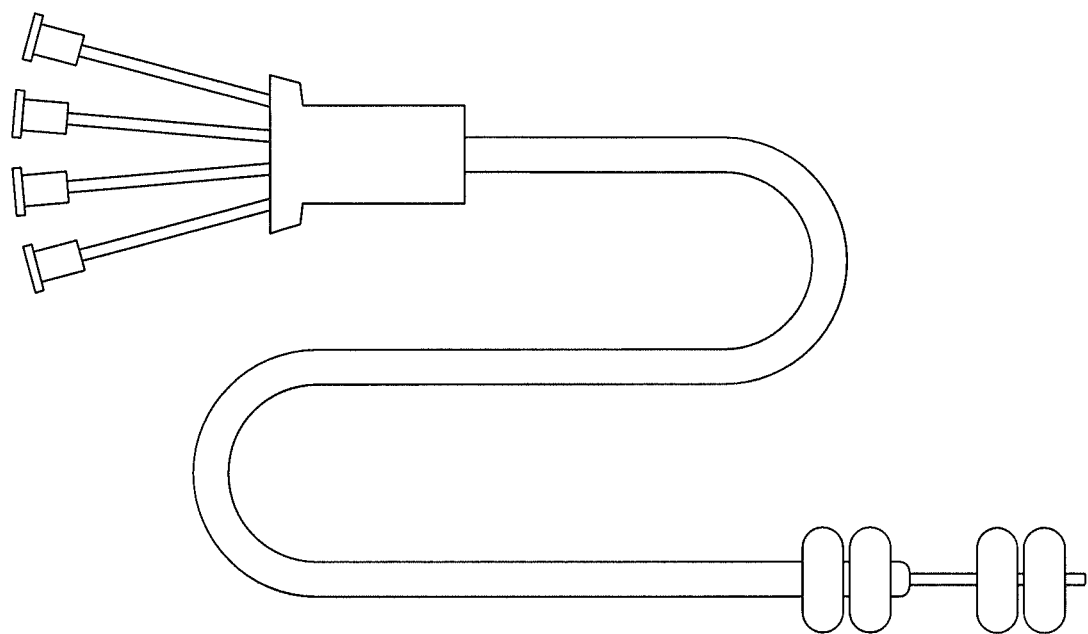
FIG. 15 illustrates an exemplary configuration of catheter device configured with an adapter.

Referring to FIG. 15, an exemplary configuration of a catheter device 416 that utilizes an adapter 412 in lieu of a console 12/handpiece 14. While catheter device 416 is referred to, it is understood that this configuration may apply to any of the catheter devices disclosed herein. The catheter device 416 includes dilation balloons 424a-424b and 426a-426b, which are carried by first and second catheters 417, 419 in a similar manner as described above in connection with catheter devices 116, 216. Balloons 424a-424b, 426a-426b are illustrated as inflated in FIG. 15, merely for ease of illustration.

Adapter 412 includes a plurality of ports extending from a proximal end 413 thereof. A proximal end 415 of the catheter device 416 is connected to a distal end of the adapter 412. The ports that may be fluidly connected to adapter 412 include, but are not limited to, balloon dilation/deflation ports 421a, vacuum ports 421b, guidewire port 421c, and an infusion (and/or aspiration) port 421d. In operation, the ports 421a-421d of adapter 412 may be attached to available aspiration, balloon dilation, fluid, and vacuum sources.

Figure 16:
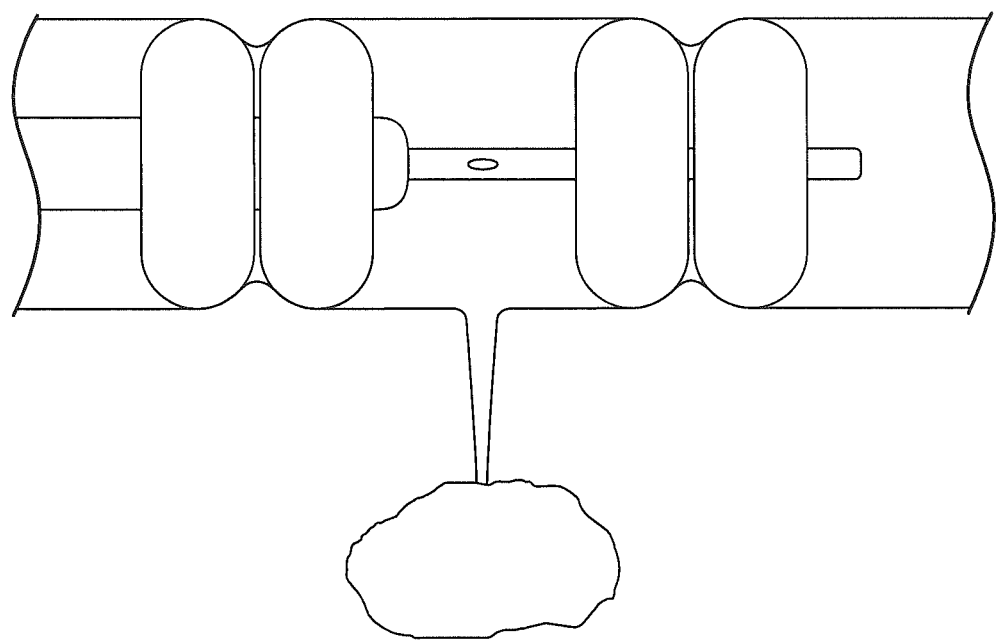
FIG. 16 illustrates an exemplary use of a catheter device to isolate a vessel.

Referring to FIG. 16, an illustration of an exemplary catheter device 416 deployed in a vessel 416 to provide a treatment directed to a tumor 500 or other tissue of interest. While catheter device 416 is referred to, it is understood that any of the catheter devices disclosed herein may be used. In the arrangement shown in FIG. 16, the balloons 424a-424b and 426a-426b are positioned on either side of a vessel, such as an artery 502. The balloons 424a-424b and 426a-426b, therefore serve to isolate the blood supply to the tumor 500 or tissue of interest. An opening 504 is provided in the first catheter 417 to provide for delivery of a fluid and/or therapeutic agent, such as, but not limited to, a chemotherapy agent, stem cells or other cancer treatment drug so as to provide targeted therapy, rather than systemic therapy.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the disclosure and that the method and apparatus within the scope of these claims and their equivalents be covered thereby. In sum, it should be understood that the disclosure is capable of modification and variation and is limited only by the following claims.

What is claimed is:

1. A treatment device, comprising:
   a first catheter and a second catheter, wherein the second catheter is at least partially disposed within the first catheter;
   at least a first pair of balloons connected to the first catheter closer to a distal end of the catheter than a proximal end of the catheter, the first pair of balloons including a first opening therebetween;
   at least a second pair of balloons spaced apart from the first pair of balloons and connected to the second catheter closer to the proximal end of the catheter than the first pair of balloons, the second pair of balloons including a second opening therebetween;
   at least one first lumen at least partially extending through the catheter, the first lumen being operatively connected to the first and second pair of balloons, wherein the at least one first lumen is configured to effect dilation and deflation the first and second pair of balloons; and
   at least one second lumen at least partially extending through the catheter, the second lumen being in communication with the first and second openings of the first pair of balloons and the second pair of balloons, wherein the second lumen is configured to deliver aspiration between the first pair and the second pair of balloons so as to create a sealed treatment region between a vessel wall and the first and second pair of balloons.

2. The treatment device of claim 1, wherein the at least one first lumen further comprises a first dilation lumen and a second dilation lumen, wherein the first dilation lumen is in communication with the first pair of balloons and wherein the second dilation lumen is in communication with the second pair of balloons.

3. The treatment device of claim 1, further comprising a third opening that is disposed within the second catheter, wherein the third opening is positioned between the first pair of balloons and the second pair of balloons, wherein the third opening is in communication with a third lumen extending through the second catheter.

4. The treatment device of claim 3, wherein the third lumen is configured to deliver a fluid to a treatment region defined between a gap created between the first pair of balloons and the second pair of balloons.

5. The treatment device of claim 4, wherein the third lumen is configured to deliver aspiration to a treatment region defined between a gap created between the first pair of balloons and the second pair of balloons.

6. The treatment device of claim 3, further comprising a fourth opening that is disposed within the second catheter, wherein the fourth opening is positioned between the first pair of balloons and the second pair of balloons, wherein the fourth opening is in communication with a fourth lumen extending through the second catheter.

7. The treatment device of claim 6, wherein the third lumen is configured to deliver a fluid to a treatment region defined between a gap created between the first pair of balloons and the second pair of balloons and wherein the fourth lumen is configured to deliver aspiration to the treatment region defined between a gap created between the first pair of balloons and the second pair of balloons.

8. The treatment device of claim 1, further comprising a guidewire lumen extending between the distal end and the proximal end of the first catheter.

9. The treatment device of claim 1, wherein either of the first and second catheters are provided with at least one marker element.

10. The treatment device of claim 9, wherein the either of the first and second catheters are provided with at least first and second marker elements, wherein the first marker element being positioned adjacent the first pair of balloons and the second marker element being position adjacent the second pair of balloons.

11. The treatment device of claim 1, wherein the second catheter is movable independently from the first catheter.

12. The treatment device of claim 1, wherein the at least one first lumen further comprises a first dilation lumen and a second dilation lumen,
wherein the first dilation lumen at least partially extends through the first catheter and is in communication with the first pair of balloons; and
wherein the second dilation lumen at least partially extends through the second catheter and is in communication with the second pair of balloons.

13. The treatment device of claim 12, further comprising a third opening that is disposed within the second catheter, wherein the third opening is positioned between the first pair of balloons and the second pair of balloons when in an installed position, wherein the third opening is in communication with a third lumen extending through the second catheter.

14. The treatment device of claim 13, wherein the third lumen is configured to deliver a fluid to a treatment region defined between a gap created between the first pair of balloons and the second pair of balloons.

15. The treatment device of claim 14, wherein the third lumen is configured to deliver aspiration to a treatment region defined between a gap created between the first pair of balloons and the second pair of balloons.

16. The treatment device of claim 13, further comprising a fourth opening that is disposed within the second catheter, wherein the fourth opening is positioned between the first pair of balloons and the second pair of balloons, wherein the fourth opening is in communication with a fourth lumen extending through the second catheter.

17. The treatment device of claim 16, wherein the third lumen is configured to deliver a fluid to a treatment region defined between a gap created between the first pair of balloons and the second pair of balloons and wherein the fourth lumen is configured to deliver aspiration to the treatment region defined between a gap created between the first pair of balloons and the second pair of balloons.

18. The treatment device of claim 1, further comprising a guidewire lumen extending between the distal end and the proximal end of the first catheter.

19. The treatment device of claim 1, further comprising an adapter connected to the proximal end of either of the first and second catheters, the adapter having at least two ports for fluidly connecting to the first and second lumens.

20. A treatment device, comprising:
a first catheter and a second catheter, wherein the second catheter is at least partially disposed within the first catheter and is selectively movable with respect to the first catheter;
at least a first pair of balloons connected to the first catheter closer to a proximal end of the catheter than a distal end of the catheter, the first pair of balloons including a first opening therebetween;
at least a second pair of balloons connected to the second catheter and positioned so as to be spaced apart from the first pair of balloons, wherein the second pair of balloons are connected to the second catheter closer to the distal end of the catheter than the first pair of balloons, the second pair of balloons including a second opening therebetween;
a first dilation lumen and a second dilation lumen,
wherein the first dilation lumen at least partially extends through the first catheter and is in communication with the first pair of balloons; and
wherein the second dilation lumen at least partially extends through the second catheter and is in communication with the second pair of balloons;
wherein the first and second dilation lumens are configured to effect selective dilation and deflation the first and second pair of balloons;
a first and second aspiration lumen,
wherein the first aspiration lumen at least partially extends through the first catheter and is in communication with a first opening that is positioned between the first pair of balloons;
wherein the second aspiration lumen at least partially extends through the second catheter and is in communication with a second opening that is positioned between the second pair of balloons;
wherein the first and second aspiration lumens are configured to deliver aspiration between the first pair and the second pair of balloons, respectively so as to create a sealed treatment region between a vessel wall and the first and second pair of balloons; and
a treatment opening that is disposed within the second catheter, wherein the treatment opening is positioned between the first pair of balloons and the second pair of balloons when in an installed position, wherein the treatment opening is in communication with a treatment lumen extending through the second catheter, wherein the treatment lumen is configured to deliver a fluid to a treatment region defined within a gap created between the first pair of balloons and the second pair of balloons.

* * * * *